(12) United States Patent
Burns et al.

(10) Patent No.: US 7,727,749 B2
(45) Date of Patent: Jun. 1, 2010

(54) STEREOSELECTIVE BIOCONVERSION OF ALIPHATIC DINITRILES INTO CYANO CARBOXYLIC ACIDS

(75) Inventors: Michael P. Burns, Mystic, CT (US);
Justin K. Weaver, Clinton, IN (US);
John Wing Wong, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 626 days.

(21) Appl. No.: 10/599,899

(22) PCT Filed: Apr. 1, 2005

(86) PCT No.: PCT/IB2005/000873
§ 371 (c)(1), (2), (4) Date: Feb. 15, 2007

(87) PCT Pub. No.: WO2005/100580
PCT Pub. Date: Oct. 27, 2005

(65) Prior Publication Data
US 2007/0196905 A1 Aug. 23, 2007

Related U.S. Application Data

(60) Provisional application No. 60/562,133, filed on Apr. 14, 2004.

(51) Int. Cl.
C12P 13/04 (2006.01)
C12P 13/00 (2006.01)
C07C 205/00 (2006.01)

(52) U.S. Cl. ........................ 435/106; 435/128; 562/553

(58) Field of Classification Search .................. 558/441; 562/401, 553; 435/106, 128
See application file for complete search history.

(56) References Cited

U.S. PATENT DOCUMENTS

| | | | |
|---|---|---|---|
| 5,593,871 A | 1/1997 | Anton et al. | |
| 5,814,508 A | 9/1998 | Dicosimo et al. | |
| 6,046,353 A | 4/2000 | Grote et al. | |
| 6,635,673 B1 | 10/2003 | Bryans et al. | |
| 6,642,398 B2 | 11/2003 | Belliotti et al. | |
| 2003/0212290 A1 | 11/2003 | Burk et al. | |
| 2004/0014195 A1 | 1/2004 | Desantis et al. | |

FOREIGN PATENT DOCUMENTS

| | | |
|---|---|---|
| WO | WO02/072856 | 9/2002 |
| WO | WO 02/095045 | 11/2002 |
| WO | WO 2004/111256 | 12/2004 |

OTHER PUBLICATIONS

International Search Report PCT/IB2005/000873.
Gavagan J E et al, "Chemoenzymic Production of Lactams from Aliphatic alpha, omega-Dinitriles", Journal of Org. Chem., V.63, No. 14, 1998, pp. 4792-4801, XP002294596.
Gavagan J E et al, "A gram-negative bacterium producing a heat-stable nitrilase highly active on aliphatic dinitriles", Applied Microbiology and Bito tech., vol. 52, 1999, pp. 654-659, XP000964621.
Almatawah et al, "Thermostable nitrilase catalysed production of nicotine acid from 3-cyanopryridine", Enzyme Microb.Technol., (1999), 718-724, vol. 25.
Cowan et al., "Biochemistry and biotechnology of mesophilic and thermophilic nitrile metaboloizing enzymes", Extremophiles, (1998), 207-216, vol. 2.
Gradley et al., "Assymmetric Hydrolysis of Chiral Nitriles by Rhodococcus Rhodochrous NCIMB 11216 Nitrilase", Biotechnology Lett., (1994), 41-46, vol. 16.
Kobayashi et al., "Enzymatic synthesis of acrylamide: a success story not yet over", Tibtech, (1992), 402-408, vol. 10.
Martinkova at al, "Synthetic Applications of Nitrile-Converting Enzymes", Current Org Chem., (2003), 1279-1295, vol. 7.
Nagasawa et al., "Nitrile Hydratase-Catalyzed Production of Nicotinamide from 3-Cyanopyridine in Rhodococcus rhodochrous J1", Appl. Environ. Microbiol., (1988), 1766-1769, vol. 54(7).
Wang et al., "Practical and Convenient Enzymatic Synthesis of Enantiopure alpha-Amino Acids and Amides", J. Org. Chem., (2002), p. 6542, vol. 67.
Wieser et al., "Stereoselective Nitrile-Converting Enzymes", Chapter in Stereoselective Biocatalysis, Marcel Dekker Inc.: New York, 2000, 461-486.
Yamamoto et al., "Efficient Conversion of Dinitrile to Mononitrile-Monocarboxylic Acid by *Corynebacterium* sp. C5 Cells during Tranexamic Acid Syntheis", J. of Ferment. Bioengineering, (1992), p. 125-129, vol. 73.

*Primary Examiner*—Taylor Victor Oh
(74) *Attorney, Agent, or Firm*—Jennifer A. Kispert; B. Timothy Creagan

(57) ABSTRACT

The present invention is directed to a regio- and stereoselective bioconversion of selected aliphatic dinitriles into corresponding cyanocarboxylic acids. More particularly, the present invention provides methods for the conversion of 2-isobutyl-succinonitrile into (S)-3 cyano-5-methylhexanoic acid, which is a useful intermediate in the synthesis of (S)-3 (aminomethyl)-5-methylhexanoic acid (pregabalin). Pregabalin can be used for treating certain cerebral diseases, for example, in the treatment and prevention of seizure disorders, pain, and psychotic disorders.

5 Claims, No Drawings

STEREOSELECTIVE BIOCONVERSION OF ALIPHATIC DINITRILES INTO CYANO CARBOXYLIC ACIDS

CROSS-REFERENCE TO RELATED APPLICATIONS

This application is a §371 National Stage filing of PCT/IB05/000873, filed Apr. 1, 2005, which claims the benefit of U.S. Provisional Application 60/562,133, filed Apr. 14, 2004, the entire contents of which are incorporated by reference.

FIELD OF THE INVENTION

The present invention is directed to novel biocatalytic processes for the regio- and stereoselective conversion of selected aliphatic dinitriles into corresponding cyanocarboxylic acids. More particularly, the present invention provides methods for the conversion of 2-isobutyl-succinonitrile into (S)-3-cyano-5-methylhexanoic acid, which is a useful intermediate in the synthesis of (S)-3-(aminomethyl)-5-methylhexanoic acid (pregabalin). Pregabalin can be used for treating certain cerebral diseases, for example, in the treatment and prevention of seizure disorders, pain, and psychotic disorders. Since pregabalin is effective in improving cerebral functions, it is also useful in the treatment of geriatric patients.

BACKGROUND OF THE INVENTION

The enzymatic hydrolysis of organic nitriles to corresponding carboxylic acids and amides provides an important alternative synthetic method to a broad spectrum of useful compounds. Conventional chemical hydrolysis of nitriles to the corresponding carboxylic acids and amides is typically carried out using a strong acid or base catalyst at high reaction temperatures making it incompatible with compounds which contain sensitive functional groups. Furthermore, the poor selectivity of chemical hydrolysis may result in unwanted by-products along with large quantities of inorganic salts. In contrast, enzymatic nitrile hydrolysis occurs under mild conditions (neutral pH, 30° C.) offering the potential for high chemo-, regio-, and stereoselectivity. As an added advantage, the formation of by-product inorganic salts is avoided.

The best-known industrial applications of nitrile-converting enzymes are the production of acrylamide (T. Nagasawa et al., *Tibtech.*, 1992, vol. 10, 402-408) and nicotinamide (T. Nagasawa et al., *Appl. Environ. Microbiol.*, 1998, vol 54, 1766-1769), using a nitrile hydratase from *Rhodococcus rhodochrous* J1. Several recent reviews (L. Martinková et al., *Current Organic Chemistry*, 2003, vol. 7, 1279-1295 and D. Cowan et al., *Extremophiles*, 1998, vol. 2, 207-216) describe the biochemistry and potential industrial applications of nitrile converting enzymes.

Enzymatic nitrile hydrolyses are catalyzed by nitrilases, which convert nitriles to the corresponding carboxylic acids, and nitrile hydratases, which convert nitriles to the corresponding amides. Amidases, which hydrolyze amides to the corresponding carboxylic acids, can be used in combination with nitrile hydratases to convert nitriles to carboxylic acids.

The use of a nitrilase enzyme to prepare a carboxylic acid from the corresponding nitrile is disclosed in WO 02/072856. Incorporation of the enzyme into a polymer matrix with cross-linking provided a catalyst with improved physical and biochemical integrity.

The regioselective preparation of ω-nitrilecarboxylic acids from aliphatic α, ω-dinitriles with a biocatalyst was disclosed in U.S. Pat. No. 5,814,508. For example, a catalyst having nitrilase activity was used to convert 2-methylglutaronitrile into 4-cyanopentanoic acid.

K. Yamamoto, et al. *J. Ferment Bioengineering*, 1992, vol. 73, 125-129 describes the use of microbial cells having both nitrile hydratase and amidase activity to convert trans 1,4-dicyanocyclohexane to trans-4-cyanocyclohexanecarboxylic acid.

Regioselective biocatalytic conversions of dinitriles to cyano substituted carboxylic acids, have been reported for a series of aliphatic α, ω-dinitrile compounds using microbial cells having an aliphatic nitrilase activity or a combination of nitrile hydratase and amidase activities (J. E. Gavagan et al. *J. Org. Chem.*, 1998, vol. 63, 4792-4801).

Stereoselective enzymatic conversions of nitriles have been described for the preparation of chiral carboxylic acids and amides enriched in one enantiomer (M Wieser et al., *Chapter in Stereoselective Biocatalysis*, Marcel Dekker Inc.: New York, 2000, 461-486). A stereoselective nitrilase enzyme from *Alcaligenes faecalis* ATCC 8750 is used to prepare (R)-mandelic acid from racemic mandelonitrile (K. Yamamoto et al., *Appl. Environ. Microbiol.*, 1991, vol. 57, 3028-3032). A nitrilase from *Rhodococcus rhodochrous* NCIMB 11216 preferentially hydrolyzes (+)-2-methylhexanitrile in a racemic mixture of 2-methylhexanitrile leaving (−)-2-methylhexanitrile unreacted (M. Gradley et al., *Biotechnology Lett.*, 1994, vol. 16, 41-46). U.S. Pat. No. 5,593,871 disclosed a process for preparing 2-alkanoic acid amides enriched in one enantiomer, from nitriles using microorganisms containing stereoselective nitrile hydratases. Enantiopure α-amino acids and amides were prepared from racemic α-aryl and α-alkyl-substituted glycine nitriles using *Rhodococcus* sp. AJ270 containing a stereoselective nitrile hydratase and a stereoselective amidase (M.-C. Wang et al., *J. Org. Chem.*, 2002, vol. 67, 6542). The foregoing references are hereby incorporated herein in their entirety.

The therapeutic value of racemic pregabalin, particularly its efficacy as an anticonvulsant, has been found to be attributable primarily to the (S)-enantiomer. Toward the goal of providing cost-effective pregabalin drug therapy, a number of synthetic routes to the (S)-enantiomer enriched compound have been investigated. For example, asymmetric hydrogenation of the appropriate cyano substituted olefin followed by reduction of the cyano group to the corresponding amine provides pregabalin substantially enriched in the (S) enantiomer (United States Patent Application Publication No. 2003/0212290).

The synthesis of pregabalin, its derivatives and analogs by purely chemical methods is disclosed in U.S. Pat. Nos. 6,642,398; 6,635,673; and 6,046,353.

SUMMARY OF THE INVENTION

In the process of the present invention, regio- and stereoselective biocatalytic conversions of aliphatic dinitriles to cyanocarboxylic acids are achieved using enzyme catalysts having nitrilase activity.

The present invention relates to a novel method for preparing an (S)-enantiomer of a compound of formula I:

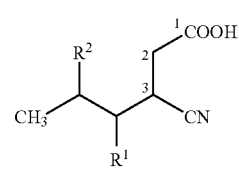

wherein C3 has an (S) configuration;

R$^1$ is hydrogen, (C$_1$-C$_6$) alkyl or phenyl; and

R$^2$ is (C$_1$-C$_8$) alkyl, (C$_2$-C$_8$) alkenyl, (C$_3$-C$_8$) cycloalkyl, —O(C$_1$-C$_6$) alkyl, —CH$_2$—CH$_2$—O— (C$_1$-C$_6$)alkyl, (C$_1$-

$C_6$)alkyl-OH, -phenyl-($C_1$-$C_6$)alkyl-OH, -phenyl-O—($C_1$-$C_6$)alkyl, phenyl or substituted phenyl;

with the proviso that when $R^2$ is methyl, $R^1$ is hydrogen, ($C_1$-$C_6$) alkyl or phenyl;

comprising the steps of:

(1a) contacting a compound of formula II:

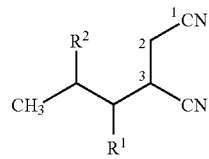

II with an enzyme catalyst having nitrilase activity in a reaction medium; and (1b) recovering the (S)-isomer of the compound of formula I from the reaction medium; and, optionally recovering unchanged (R)-isomer of compound II.

Compounds of formula I are useful in synthesizing compounds having pharmaceutical activity, such as pregabalin.

In a preferred embodiment of the invention, $R^1$ and $R^2$ are independently hydrogen or $C_1$ to $C_3$ alkyl.

In a preferred embodiment of the invention, the compound of formula II is a racemic mixture comprising 3R and 3S isomers.

A preferred embodiment of the present invention is the process whereby racemic 2-isobutyl-succinonitrile (the compound of formula II wherein $R^1$ is H and $R^2$ is methyl) is converted into (S)-3-cyano-5-methylhexanoic acid (the compound of formula I wherein $R^1$ is H and $R^2$ is methyl) comprising the steps of:

(2a) contacting racemic 2-isobutyl-succinonitrile with an enzyme catalyst having nitrilase activity in a reaction medium; and (2b) recovering (S)-3-cyano-5-methylhexanoic acid from the aqueous mixture; and, optionally recovering unchanged (R)-2-isobutylsuccinonitrile.

Preferably the reaction medium is an aqueous medium.

In a preferred embodiment of the present invention, the recovered and unchanged (R)-isomer of compound II is subsequently racemized by heating with a weak base in the presence of an organic solvent. A preferred base is 1,8-diazabicyclo[5.4.0.]undec-7-ene and a preferred solvent is toluene. Optionally the resulting racemate of II may be recycled into either of the above stated processes at step (1a) or (2a).

In one embodiment of the present invention the enzyme catalyst is in the form of whole microbial cells, extracts of microbial cells, partially purified enzymes, purified enzymes or enzyme catalysts that are immobilized on a support.

In another embodiment of the present invention, the enzyme catalyst is a partially purified enzyme. Examples of partially purified enzymes include, but are not limited to NIT-101, NIT-102, NIT-103 (BioCatalytics Inc., Pasadena, Calif.), and nitrilase from *Arabidopsis thaliana* (Jülich Fine Chemicals, Jülich, Germany).

In a preferred embodiment of the present invention the nitrilase enzyme catalyst is immobilized on a support. Examples of immobilized nitrilase enzyme catalysts include but are not limited to NIT-102 C2 (BioCatalytics Inc., Pasadena, Calif.), NIT-102 immobilized on Eupergit (Röhm GmbH & Co. KG, Darmstadt, Germany), and nitrilase from *Arabidopsis thaliana* immobilized on Eupergit. In a preferred embodiment the immobilized nitrilase enzyme catalyst is NIT-102 C2.

In another embodiment, the reaction media is comprised of distilled water or buffered water. Preferably the buffered water is buffered to a pH in the range of about 5.0 to about 10.0 and most preferably to a pH in the range of about 6.0 to about 8.0.

The present invention also relates to a process for the preparation of (S)-3-(aminomethyl)-5-methylhexanoic acid (pregabalin) comprising the steps of:

(a) contacting racemic 2-isobutyl-succinonitrile with an enzyme catalyst having nitrilase activity in a reaction medium;

(b) recovering (S)-3-cyano-5-methylhexanoic acid from the reaction medium;

(c) converting (S)-3-cyano-5-methylhexanoic acid into an acid salt; and (d) hydrogenating the acid salt to form (S)-3-(aminomethyl)-5-methylhexanoic acid (pregabalin).

Preferably, the acid salt has the formula

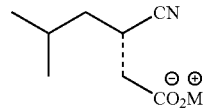

wherein M is Na, K, Li, $NH_4$, $NH_2R^6R^7$, $NH_3R^1$ or $NH(R^6)_2R^7$ wherein $R^6$ and $R^7$ are each independently ($C_1$-$C_6$) alkyl.

For convenience, certain terms employed in the specification, examples and appendant claims are collected here. Unless defined otherwise, all technical and scientific terms used herein have the same meaning as commonly understood by one of ordinary skill in the art to which this invention belongs.

The term "alkyl" is a straight or branched group of from 1 to 8 carbon atoms including but not limited to methyl, ethyl, propyl, butyl, iso-butyl, and tert-butyl.

The term "cycloalkyl" as used herein includes moieties derived from cyclic hydrocarbons containing from three to seven ring carbon atoms, including cyclic hydrocarbon moieties substituted with straight or branched alkyl moieties.

The term "alkoxy", as used herein, means "alkyl-O—", wherein "alkyl" is defined as above.

The term "alkenyl" is intended to include hydrocarbon chains of either a straight or branched configuration comprising one or more carbon-carbon double bonds which may occur in any stable point along the chain, such as ethenyl and propenyl. Alkenyl groups typically will have 2 to about 12 carbon atoms, more typically 2 to about 8 carbon atoms.

The term racemate, as used herein, means an equimolar mixture of a pair of enantiomers. A racemate is usually formed when synthesis results in the generation of a stereocenter. As used herein, the term racemic mixture means racemate.

As used herein, the term enantiomers refers to compounds which at the molecular level are nonsuperposable with mirror images of each other. Enantiomers may exist in either the (R) or (S) configuration.

As used herein, the term stereoselective synthesis refers to a chemical reaction that leads to formation of a single stereoisomer or an enantiomer-enriched mixture of isomers from among two or more possible stereoisomers.

As used herein, the term regioselective refers to a reaction that takes place at a single atom or group of atoms from among two or more possible atoms or groups of atoms. The regioselective hydrolysis of a dinitrile results in the conversion of a single nitrile group to a carboxyl group.

"° C." means degrees-Celsius;

The term "enzyme catalyst", as used herein, means a catalyst which is characterized by either a nitrilase activity or a combination of a nitrile hydratase activity and an amidase activity. The catalyst may be in the form of a whole microbial cell, permeabilized microbial cell(s), one or more cell component of a microbial cell extract, partially purified enzyme(s), or purified enzyme(s).

As used herein, the term enantiomer excess refers to the mole fraction of the dominant enantiomer in a mixture of enantiomers expressed as a percentage.

The term "aqueous reaction mixture" means a mixture of the substrate and enzyme catalyst in a largely aqueous medium.

The term "nitrilase activity" means an enzyme activity that converts a nitrile group to a carboxylic acid group.

The term "nitrile hydratase activity" as used herein, means an enzyme activity that converts a nitrile group to an amide group.

The term "amidase activity" means an enzyme activity that converts an amide group to a carboxylic acid group.

ATCC is American Type Culture Collection located at 10801 University Boulevard, Manassas, Va., 20110-2209, U.S.A. BioCatalytics Inc. is located at 129 N. Hill Avenue, Suite 103, Pasadena, Calif., 91106, U.S.A. Jülich Fine Chemicals GmbH is located at Rudolf-Schulten-Straße 5, D-52428 Jülich, Germany.

DETAILED DESCRIPTION OF THE INVENTION

The present invention provides an enzymatic method for preparing aliphatic cyanocarboxylic acids of formula I from dinitriles of formula II. Any suitable method commonly used in the art may be used to prepare the dinitrile (II) starting materials.

Scheme 1 refers to a specific embodiment of the present invention wherein a chemo-enzymatic method is used in the conversion of 2-isobutyl-succinonitrile (V) into (S)-3-cyano-5-methylhexanoic acid (VI). Compound VI may be used as an intermediate in the synthesis of pregabalin (VII) as illustrated in Scheme 2. Step 3 of Scheme 1 depicts the racemization of by-product (R)-isomer (Va) and subsequent recycle into Step 2.

In Step 1 of Scheme 1 racemic 2-isobutyl-succinonitrile (V) is formed by the condensation of isovaleraldehyde (III) with ethylcyanoacetate (IV) followed by the addition of KCN. The racemate arises from the stereocenter created at the $C_3$ carbon atom of V.

Step 2 of Scheme 1 depicts the regio- and stereoselective hydrolysis of the dinitrile V racemate yielding (S)-3-cyano-5-methylhexanoic acid (VI) plus unchanged (R)-isomer of V.

The nitrilase catalyzed hydrolysis of 2-isobutyl-succinonitrile (V) into (S)-3-cyano-5-methylhexanoic acid VI is both regioselective and stereoselective. Regioselectivity is based upon conversion of the cyano group into a carboxyl group at the C1 carbon atom only. The reaction is stereoselective in that the (S) enantiomer of V is predominantly involved in the conversion leaving the (R)-enantiomer essentially unchanged.

As illustrated in Scheme 2, an acid salt VIa of S-cyanoacid VI is hydrogenated in a subsequent step to obtain (S)-3-(aminomethyl)-5-methylhexanoic acid (pregabalin). The reaction is carried out in the presence of a hydrogenation catalyst, preferably Raney nickel. Acceptable acid salts include compounds of formula VIa wherein M is Na, K, Li, $NH_4$, $NH_2R^6R^7$, $NH_3R^6$ or $NH(R^6)_2R^7$ wherein $R^6$ and $R^7$ are independently $(C_1-C_6)$alkyl.

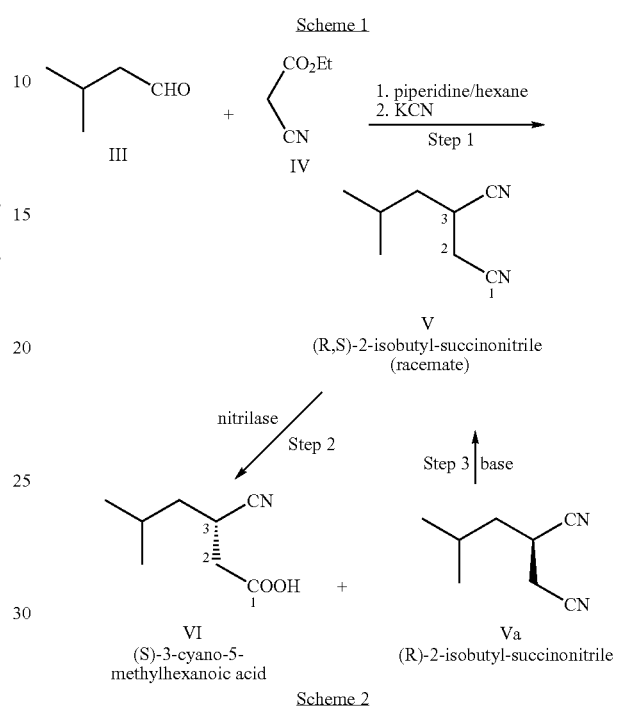

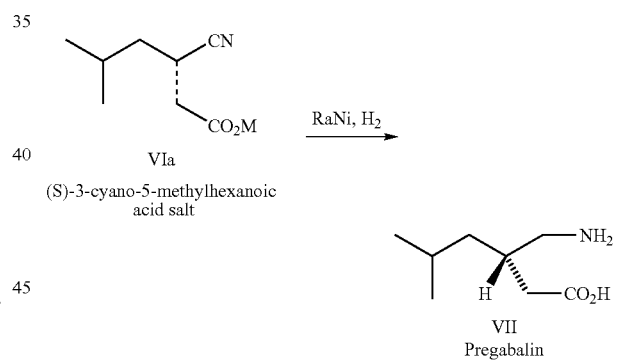

In the regio- and stereoselective conversion of racemate V into (S)-cyanoacid VI, as depicted in Scheme 1, the nitrilase enzyme reacts predominantly with the (S) enantiomer. Accordingly the reaction mixture is increasingly enriched in the (R) enantiomer Va as the conversion progresses.

Another objective of the current invention is to avoid economic waste by recycling or reusing the unchanged (R)-dinitrile Va. The present invention, therefore, provides a method for the racemization of the (R)-dinitrile (Step 3, Scheme 1) and subsequent recycle through Step 2 of Scheme 1.

Various enzymes of the present invention, having nitrilase activity or a combination of nitrile hydratase and amidase activities, can be found through screening protocols such as enrichment isolation techniques, which initially select microorganisms based on their ability to grow in media containing the enriched nitrile. Enrichment isolation techniques typically involve the use of carbon-limited or nitrogen-limited media supplemented with an enrichment nitrile, which can be the nitrile substrate for the desired bioconversion, or a structurally similar nitrile compound. Microorganisms that possess nitrilase activity can be initially selected based on their ability to grow in media containing the enrichment nitrile. Gavagan et al., (*Appl. Microbiol. Biotechnol.* (1999) vol. 52, 654-659) used enrichment techniques to isolate a Gram-negative bacterium, *Acidovorax facilis* 72W (ATCC 55746), from soil, using 2-ethylsuccinonitrile as the sole nitrogen source. *Acidovorax facilis* 72W (ATCC 55746) was shown to be useful for the selective conversion of 2-methylglutaronitrile to 4-cyanopentanoic acid. Enrichment techniques were also used to isolate the thermophilic bacterium, *Bacillus pallidus* Dac521, which catalyzes the conversion of 3-cyanopyridine to nicotinic acid (Almatawah and Cowan, *Enzyme Microb. Technol.* (1999) vol. 25, 718-724). Microorganisms isolated by enrichment techniques can be tested for nitrile hydrolysis activity by contacting suspensions of microbial cells with a nitrile compound and testing for the presence of the corresponding carboxylic acid using analytical methods such as high performance liquid chromatography, gas liquid chromatography, or liquid chromatography mass spectrometry (LCMS). Techniques for testing the nitrile hydrolysis activity of *Acidovorax facilis* 72W (ATCC 55746) are reported in U.S. Pat. No. 5,814,508.

Once a microorganism having nitrilase activity or nitrile hydratase and amidase activities has been isolated, enzyme engineering can be employed to improve various aspects of the enzyme(s). These improvements can be useful for the present invention and include increasing selectivity, catalytic efficiency of the enzyme, stability to higher temperatures and a wider range of pH, and enabling the enzyme to operate in a reaction medium including a mixture of aqueous buffer and organic solvent.

A variety of techniques, which can be employed in the present invention, to produce an enzyme catalyst having nitrilase activity or nitrile hydratase and amidase activities in addition to having an improved yield, throughput, and product quality suitable for a particular bioconversion process, include but are not limited to enzyme engineering techniques such as rational design methods which include site-directed mutagenesis, and directed evolution techniques utilizing random mutagenesis or DNA shuffling techniques.

Suitable enzyme catalysts for the conversion of compounds of formula II into compounds of formula I are in the form of whole microbial cells, permeabilized microbial cells, extracts of microbial cells, partially purified enzymes or purified enzymes, and such catalysts can be immobilized on a support.

This process can be carried out in a single phase by contacting 2-isobutyl-succinonitrile with an enzyme catalyst in distilled water, or in an aqueous solution of a buffer, which will maintain the initial pH of the reaction between 5.0 and 10.0, preferably between 6.0 and 8.0. Suitable buffering agents include potassium phosphate and calcium acetate. As the reaction proceeds, the pH of the reaction mixture may change due to the formation of an ammonium salt of the carboxylic acid from the corresponding nitrile functionality of the dinitrile. The reaction can be run with no pH control, or a suitable acid or base can be added over the course of the reaction to maintain the desired pH. However, as indicated above it is possible to produce enzyme catalysts using technologies such as enzyme engineering and directed evolution, which will operate effectively over wider pH ranges.

This process can be carried out in reaction mixtures comprised of two phases: an aqueous phase, which initially contains enzyme and dissolved 2-isobutyl-succinonitrile, and an organic phase, which consist mainly of racemic 2-isobutyl-succinonitrile. Two-phase reaction mixtures are prepared by adding 2-isobutyl-succinonitrile to an aqueous solution of enzyme and buffer agents such that the amount of 2-isobutyl-succinonitrile added exceeds it aqueous solubility limit. The aqueous solubility limit of 2-isobutyl-succinonitrile in 50 mM potassium phosphate (30° C., pH 7.5) is approximately 0.06M. Over the course of the reaction, (S)-3-cyano-5-methylhexanoic acid ammonium salt is formed and increases in concentration in the aqueous phase, while the organic phase decreases in volume and becomes enriched in (R)-2-isobutyl-succinonitrile. Alternately, this process can also be carried out in reaction mixtures comprised of three phases: an aqueous phase, which initially contains dissolved 2-isobutyl-succinonitrile, an organic phase, which consists mainly of racemic 2-isobutyl-succinonitrile, and a solid phase, which consists of enzyme immobilized on an insoluble support. Three-phase reaction mixtures are prepared by the procedure described for two-phase reaction mixture except that an enzyme immobilized on an insoluble support is used in place of an un-immobilized enzyme.

Optionally, the enzyme may be immobilized in a polymer matrix or an insoluble support. Immobilized enzyme catalysts can be used repeatedly and in continuous processes, and can be separated from the products of the enzymatic process more easily than un-immobilized enzyme catalysts. Methods for the immobilization of enzymes in a polymer matrix, such as calcium alginate or polyacrylamide, or an insoluble support, such as celite, are well known to those skilled-in-the-art. NIT-102 C2 (BioCatalytics Inc., Pasadena, Calif.), which is a nitrilase enzyme immobilized on an insoluble support, is particularly useful for the conversion of II to III, since it can be used repeatedly in batch or continuous processes. The concentration of NIT-102 C2 used in a reaction is chosen to obtain a desired reaction rate and depends on the specific activity of the catalyst and the concentration of substrate. Typically, NIT-102 C2 is used in the range of about 0.001 g to 0.3 g moist weight per mL of reaction volume, with a preferred range of 0.01 to 0.15 g moist weight per mL of reaction volume.

Additionally, several lyophilized lysates prepared from microbial cells and designated as NIT-101, NIT-102, NIT-103 (BioCatalytics Inc., Pasadena, Calif.), and nitrilase from *Arabidopsis thaliana* (Jülich Fine Chemicals, Jülich, Germany) are also useful for the conversion of II to III. Contact of NIT-101, NIT-102, NIT-103 and *A. thaliana* nitrilase with I in an aqueous reaction mixture results in the formation of II. Reactions using NIT-101, NIT-102, NIT-103 and nitrilase from *Arabidopsis thaliana*, can be carried out in two-phase reaction mixtures using catalyst concentrations ranging from 0.001-0.04 g dry weight per ml reaction volume, with a preferred range of 0.002-0.02 g dry weight per mL reaction volume.

The temperature of the hydrolysis reaction is chosen to both optimize the reaction rate and the stability of the enzyme catalyst activity. The temperature of the reaction may range from just above the freezing point of the suspension (ca. 0° C.) to 60° C., with a preferred range of reaction temperature from 5° C. to 35° C.

Recovery of the (3S) isomer of the compound of formula I and recovery of unchanged (3R) isomer of the compound of formula II may be carried out using suitable separation, isolation and purification techniques well-known to those skilled in the art.

In a preferred method of recovery, the unchanged (3R) isomer of the compound of formula II is separated from the basic aqueous reaction mixture by extraction with an organic solvent such as ethyl acetate. The acid salt of the (3S) isomer of the compound of formula I is preferentially dissolved in the aqueous layer and is subsequently isolated by acidification and extraction with an organic solvent such as ethyl acetate.

The compounds of formula I can be used to synthesize compounds, such as pregabalin, having usefulness in the treatment of such disorders as epilepsy, convulsion, anxiety, pain, and neurodegenerative disorders, including Alzeimer's disease, Huntington's disease and Parkinson's disease.

Examples of specific compounds of formula I are the following compounds:
(S)-3-cyano-5-methyl-octanoic acid;
(S)-3-cyano-5-methyl-heptanoic acid;
(S)-3-cyano-5-methyl-hexanoic acid;
(S)-3-cyano-5-methyl-nonanoic acid;
(S)-3-cyano-5-ethoxy-hexanoic acid;
(S)-3-cyano-5-cyclohexyl-hexanoic acid; and
(S)-3-cyano-5-trifluoromethyl-hexanoic acid.

Example 1

Preparation of 2-isobutyl-succinonitrile

A mixture of ethyl cyanoacetate (73.3 g, 6.48 mol), isovaleraldehyde (613.9 g, 7.13 mol), piperidine (5.5 g, 0.065 mol), and hexane (0.5 L) was placed under reflux with continuous removal of water. When no additional water was collected, the mixture was cooled and distilled under vacuum to remove solvent. Isopropanol (1 L) was added to the remaining oil, followed by a solution of potassium cyanide (422 g, 6.48 mol) in water (2 L). The reaction mixture was maintained below 35° C. during addition of the potassium cyanide solution and then held at approximately 35° C. for 4 h. The reaction mixture was distilled at atmospheric pressure until a temperature of 95° C. was reached and then refluxed at this temperature for 5 h. The reaction mixture was cooled, diluted with water (0.5 L) and extracted with 1 L methyl tert-butyl ether (MTBE). The MTBE extract was washed with water (0.5 L), dried over anhydrous magnesium sulfate, filtered, and concentrated under vacuum to give 873.4 g of 2-isobutyl-succinonitrile as an oil. Purified samples of 2-isobutyl-succinonitrile can be obtained by vacuum distillation (90° C. at 0.275 mm Hg).

$^1$H NMR (CDCl$_3$, 400 MHz): δ 0.93-0.99 (m, 6H), 1.43-1.50 (m, 1H), 1.71-1.78 (m, 1H), 1.81-1.91 (m, 1H), 2.69 (d, 2H, J=6.5 Hz), 2.90-2.97 (m, 1H).

Example 2

Preparation of (S)-3-Cyano-5-methylhexanoic Acid from 2-isobutyl-succinonitrile with NIT-101, NIT-102. NIT-103, and *Arabidopsis thaliana* nitrilase Three 8 mL screw-cap glass vials were each charged with 2-isobutyl-succinonitrile (20 mg), 1 mL of 50 mM potassium phosphate buffer (pH 7.5, 2 mM dithiothreitol (DTT)), and 10 mg of a nitrilase enzyme selected from NIT-101, NIT-102, or NIT-103 (Biocatalytics Inc., Pasadena, Calif.). One 8 mL screw-cap glass vial was charged with 2-isobutyl-succinonitrile (20 mg) and 1 mL of a solution of *Arabidopsis thaliana* nitrilase in 50 mM phosphate buffer (pH 7.8) containing 100 mM ethylenediaminetetraacetic acid (EDTA) and 2 mM DTT (Jülich Fine Chemicals, Jülich, Germany). The four reaction mixtures were stirred with magnetic stir-bars for 15 h at 30° C. and then individually extracted with ethyl acetate (2×6 mL). After removing the ethyl acetate extracts, the aqueous parts were treated with 4N HCl (0.15 mL) and extracted with ethyl acetate (3×6 mL). Ethyl acetate extracts of the acidified aqueous parts were concentrated under vacuum to give 7.8 mg (34.2% yield), 8.8 mg (38.6% yield), 8.1 mg (35.5% yield), and 4.0 mg (17.5% yield) of (S)-3-cyano-5-methylhexanoic acid ((S)-CMHA) for the reactions performed with NIT-101, NIT-102, NIT-103, and *A. thaliana* nitrilase, respectively. Samples of (S)-3-cyano-5-methylhexanoic acid from each of the reactions were treated with an excess of (trimethylsilyl)diazomethane to give their methyl ester derivatives and analyzed by gas chromatography (GC) on a Chiraldex™ G-TA column (30 M×0.25 mm ID, 125 micron film thickness) to determine enantiomeric purities. The enantiomeric purities of the NIT-101, NIT-102, NIT-103, and *A. thaliana* nitrilase reaction products were 96.3%, 91.1%, 95.5%, and 98.5% e.e., respectively. (e.e. means "enantiomer excess")

Example 3

Preparation of (S)-3-Cyano-5-methylhexanoic Acid from 2-isobutyl-succinonitrile with NIT-102

A 125 mL jacketed reaction vessel maintained at 30° C. was charged with 2-isobutyl-succinonitrile (3.33 g), NIT-102 (0.5 g) and 122 mL of 50 mM potassium phosphate buffer (pH 7.5) containing 5 mM DTT and 1 mM EDTA (reaction buffer). After stirring for 12.5 h, the product mixture was extracted with ethyl acetate (4×50 mL). The ethyl acetate extracts were removed, and the aqueous part was adjusted to pH 2.5 with 4M HCl and extracted with ethyl acetate (3×50 mL). The ethyl acetate extracts of the acidified aqueous part were combined, dried with anhydrous MgSO$_4$, filtered, and concentrated under vacuum to give 1.56 g of (S)-CMHA (41.1%). A sample of the reaction product was treated with (trimethylsilyl)diazomethane and analyzed by GC as described in example 2 to reveal an enantiomeric purity of 98.5% e.e.

$^1$H NMR (CDCl$_3$, 400 MHz): δ 0.93-0.97 (m, 6H), 1.30-1.37 (m, 1H), 1.61-1.68 (m, 1H), 1.82-1.89 (m, 1H), 2.57-2.63 (m, 1H), 2.72-2.78 (m, 1H), 2.98-3.06 (m, 1H).

Example 4

Preparation of Potassium (S)-3-Cyano-5-methylhexanoate from 2-Isobutyl-succinonitrile with NIT-102 C2

Two 125 mL jacketed reaction vessels maintained at 30° C. were each charged with 2-isobutyl-succinonitrile (6.81 g), NIT-102 C2 (1.70 g) and 118.2 mL of reaction buffer. After stirring for 24 h, the product mixtures were decanted, leaving the enzyme catalyst in the reaction vessels. Reaction buffer (20 mL) was added to the each reaction vessel, stirred for approximately 2 min., and then decanted and added to the product mixtures. Reactions were repeated by adding 2-isobutyl-succinonitrile (6.81 g) and reaction buffer (118.2 mL) to each reaction vessel and stirring the reaction mixtures for 24 h. After four reactions were completed in each vessel (total of eight batch reactions), the product mixtures were combined and extracted with MTBE (3×500 mL). The MTBE extracts were removed and the aqueous part adjusted to pH 2.1 with phosphoric acid and extracted with MTBE (2×500 mL). The MTBE extract of the acidified aqueous part was concentrated under vacuum to leave an oil, which was treated with water (100 mL) and KOH (8.5 g). The resulting solution was concentrated under vacuum to give 24.2 g (31.3%) of potassium (S)-3-cyano-5-methylhexanoate. Methyl (S)-3-cyano-5-methylhexanoate was prepared from potassium (S)-

3-cyano-5-methylhexanoate and analyzed by chiral GC to reveal an enantiomeric purity of 99.1% e.e.

$^1$H NMR (D$_2$O, 400 MHz): δ 0.75-0.78 (m, 6H), 1.18-1.25 (m, 1H), 1.43-1.50 (m, 1H), 1.53-1.68 (m, 1H), 2.28-2.38 (d, 2H, J=6.5 Hz), 2.86-2.93 (m, 1H).

Example 5

Preparation of (S)-3-Cyano-5-methylhexanoic Acid from 2-Isobutyl-succinonitrile with NIT-102 C2 Under Nitrogen Atmosphere A 125 mL jacketed reaction vessel maintained at 30° C. was charged with 2-isobutyl-succinonitrile (6.53 g), NIT-102 C2 (2.61 g), 120 g of reaction buffer, and purged with nitrogen. The resulting mixture was stirred for 24 h and then decanted to a 250 mL glass bottle, leaving the catalyst in the reaction vessel. The reaction was repeated by recharging the reaction vessel containing the used catalyst with 2-isobutyl-succinonitrile (6.53 g) and 120 g of reaction buffer, purging with nitrogen, and stirring the resulting mixture for 24 h. Reaction samples (0.1 mL) were mixed with 0.4 mL of water:methanol:trifluoroacetic acid (60:40:0.09, v/v/v) and analyzed by HPLC on a Symmetry™ C8 column (150×3.9 mm) maintained at 30° C. The column was eluted with water:methanol:trifluoroacetic acid (60:40:0.09, v/v/v) and detection was carried out with a refractive index detector.

A total of fifty batch reactions were carried out with catalyst recycle. Product mixtures from two consecutive batch reactions were combined and extracted with ethyl acetate (2×150 mL). The aqueous part was then adjusted to pH 2 with 4M HCl and extracted with ethyl acetate (2×150 mL). The ethyl acetate extracts of the acidified aqueous part were combined, dried over anhydrous magnesium sulfate, filtered, and concentrated under vacuum to yield (S)-CMHA. A total of 160.8 g (43.2% yield) of (S)-CMHA was obtained from fifty batch reactions. Initial rates for reactions one, twenty-six, and fifty, were 14.8, 17.4, and 15.1 mM (S)-CMHA/h, respectively. Chiral GC analysis of the methyl ester derivative of (S)-CMHA isolated from batch reactions 39 to 50 revealed an average enantiomeric purity of 99.0% e.e.

Example 6

Preparation of (S)-3-Cyano-5-methylhexanoic Acid from 2-Isobutyl-succinonitrile with NIT-102 C2 Under Ambient Atmosphere A series of batch reactions for the conversion of 2-isobutyl-succinonitrile to (S)-CMHA using NIT-102 C2 was carried out as described in example 5 except that reactions were carried out under ambient atmosphere instead of nitrogen atmosphere. Reaction samples were analyzed by HPLC as described in example 5.

A total of fifty batch reactions were carried out with catalyst recycle under ambient atmosphere. Initial reaction rates determined from reaction samples taken at four hours were 14.2, 13.2 and 9.3 mM (S)-CMHA/h for reactions one, twenty-six, and fifty, respectively.

Example 7

Preparation of tert-Butylammonium (S)-3-Cyano-5-methylhexanoate

Product mixtures from the conversion of 2-isobutyl-succinonitrile to (S)-CMHA (Example 6, reactions 37-44) were combined and extracted with ethyl acetate (2×250 mL). The ethyl acetate extracts were dried over anhydrous magnesium sulfate, filtered and concentrated under vacuum to give an oil (32.5 g, 62.2% yield) that was mainly (R)-2-isobutyl-succinonitrile. The aqueous part was adjusted to pH 2 with 4M HCl and extracted with ethyl acetate (2×250 mL). The ethyl acetate extracts were concentrated to a volume of 470 mL and then stirred while tert-butylamine (15.9 mL, 151.5 mmol) was added dropwise. The white crystalline salt that formed was collected by filtration and air-dried overnight to give 30.0 g of t-butylammonium (S)-3-cyano-5-methylhexanoate. Methyl (S)-3-cyano-5-methylhexanoate was prepared from t-butylammonium (S)-3-cyano-5-methylhexanoate and analyzed by chiral GC to reveal an enantiomeric purity of 99.5% e.e.

$^1$H NMR (CDCl$_3$, 400 MHz): δ 0.90-0.94 (m, 6H), 1.26-1.32 (m, 10H), 1.54-1.61 (m, 1H), 1.78-1.88 (m, 1H), 2.30-2.35 (m. 1H), 2.43-2.50 (m, 1H), 2.96-3.04 (m, 1H).

Example 8

Preparation of (S)-3-Aminomethyl-5-Methylhexanoic Acid from Potassium (S)-3-Cyano-5-Methylhexanoate A mixture of potassium (S)-3-cyano-5-methylhexanoate (20 g, 103.5 mmol), water (50 mL), 45% KOH (12 g), isopropanol (12 g), and Raney Nickel were shaken overnight in a Parr Shaker under 50 psi of hydrogen. The mixture was filtered, heated to approximately 50° C., treated with acetic acid (6.5 mL) and stirred overnight at room temperature. The mixture was then adjusted to slightly above pH 7 with 45% KOH and concentrated under vacuum to remove most of the isopropanol. Isopropanol (20 mL) was added to the mixture, which was then acidified with acetic acid, stirred overnight at room temperature, and filtered to give 4.3 g of (S)-3-aminomethyl-5-methylhexanoic acid as a white crystalline solid. The enantiomeric purity was determined to be 100% e.e. by preparing a derivative of (S)-3-aminomethyl-5-methylhexanoic acid using Marfey's reagent (Nα-(2,4-dinitro-5-fluorophenyl)-L-alaninamide) and analyzing by HPLC on a BDS Hypersil C18 column (250×4.6 mm, 5μ) eluted with acetonitrile:1% triethylamine (pH 3) (38:62, v/v).

Example 9

Preparation of (S)-3-Aminomethyl-5-Methylhexanoic Acid from t-Butylammonium (S)-3-Cyano-5-Methylhexanoate A mixture of t-butylammonium (S)-3-cyano-5-methylhexanoate (26 g, 113.9 mmol), water (48.8 mL), ethanol (35.8 mL), KOH (7.2 g, 91% flake), and Sponge Nickel™ (A-7000, 16.3 g water wet, Activated Metals & Chemicals, Inc., Sevierville, Tenn.) was shaken overnight in a Parr Shaker under 50 psi of hydrogen. The mixture was filtered (celite) and the cake washed with water (10 mL) and ethanol (5 mL). Acetic acid (9.4 mL) was added to the filtrate and the resulting mixture was stirred overnight at 4° C. The product was filtered, rinsed with 10 mL of isopropyl alcohol, and dried under vacuum to give 11.1 g (61%) of a white solid. A portion (10.0 g) of this material was crystallized from a 1:1 mixture of isopropyl alcohol and water to give 8.8 g of (S)-3-aminomethyl-5-methylhexanoic acid in 100% ee.

Example 10

Racemization of (R)-2-Isobutyl-succinonitrile Using DBU

The racemization of (R)-2-isobutyl-succinonitrile was carried out on material recovered from bioconversion of racemic 2-isobutyl-succinonitrile with NIT-102 C2. A mixture of (R)-2-isobutyl-succinonitrile (1.36 g, 10 mmol, 69% ee), toluene (5 mL) and 1,8-diazabicyclo[5.4.0]undec-7-ene (DBU, 0.076 g, 5 mmol) was refluxed for 2 h. Water (10 mL) was added to the reaction and the resulting mixture extracted with ethyl acetate (2×10 mL). The combined organic extracts were washed sequentially with 5% HCl (20 mL) and saturated aqueous sodium chloride (20 mL), dried over anhydrous magnesium sulfate, filtered, and concentrated under vacuum to give racemic 2-isobutyl-succinonitrile (1.14 g, 84%). Enantiomeric purity was determined by GC using a Chiraldex™ G-TA column (30 M×0.25 mm ID, 125 micron film thickness).

Example 11

Racemization of (R)-2-Isobutyl-succinonitrile Using Amberlite® IRA-400

Amberlite® IRA-400 resin (1 g wet weight, Rohm & Haas, Philadelphia, Pa.) was stirred with 5% NaOH (10 mL) for 10 minutes and washed with water until the washings were neutral. Ethanol (25 mL) and (R)-2-isobutyl-succinonitrile (69% ee) were added to the resin and the resulting mixture refluxed for 2 h. The reaction mixture was filtered and concentrated under vacuum. The residue was taken up into ethyl acetate (25 mL) and washed with water (3×100 mL). The organic phase was dried over anhydrous magnesium sulfate, filtered, and concentrated under vacuum to give racemic 2-isobutyl-succinonitrile (0.81 g, 81%).

The invention claimed is:

1. A process for preparing (S)-3-(aminomethyl)-5-methylhexanoic acid (pregabalin) comprising the steps of:
    (a) contacting 2-isobutyl-succinonitrile with an enzyme catalyst having nitrilase activity in a reaction medium;
    (b) recovering (S)-3-cyano-5-methylhexanoic acid from the reaction medium;
    (c) converting (S)-3-cyano-5-methylhexanoic acid into an acid salt; and
    (d) hydrogenating the acid salt to form (S)-3-(aminomethyl)-5-methylhexanoic acid (pregabalin).

2. The process according to claim 1, wherein unchanged (R)-3-cyano-5-methylhexanoic acid is recovered from the reaction medium of step (a).

3. The process according to claim 1 wherein said unchanged (R)-3-cyano-5-methylhexanoic acid of step (a) is racemized by heating with base in the presence of an organic solvent to form racemic 2-isobutyl-succinonitrile and step (a) is repeated using said racemic 2-isobutyl-succinonitrile.

4. The method of claim 1 wherein said enzyme catalyst is a nitrilase in the form of whole microbial cells, permeabilized microbial cells, extracts of microbial cells, partially purified enzymes, purified enzymes or an enzyme catalyst immobilized on a support.

5. A method according to claim 1 wherein said enzyme catalyst is selected from the group consisting of NIT-101, NIT-102, NIT-103 and nitrilase from *Arabidopsis thaliana*.

* * * * *